Figure 1:
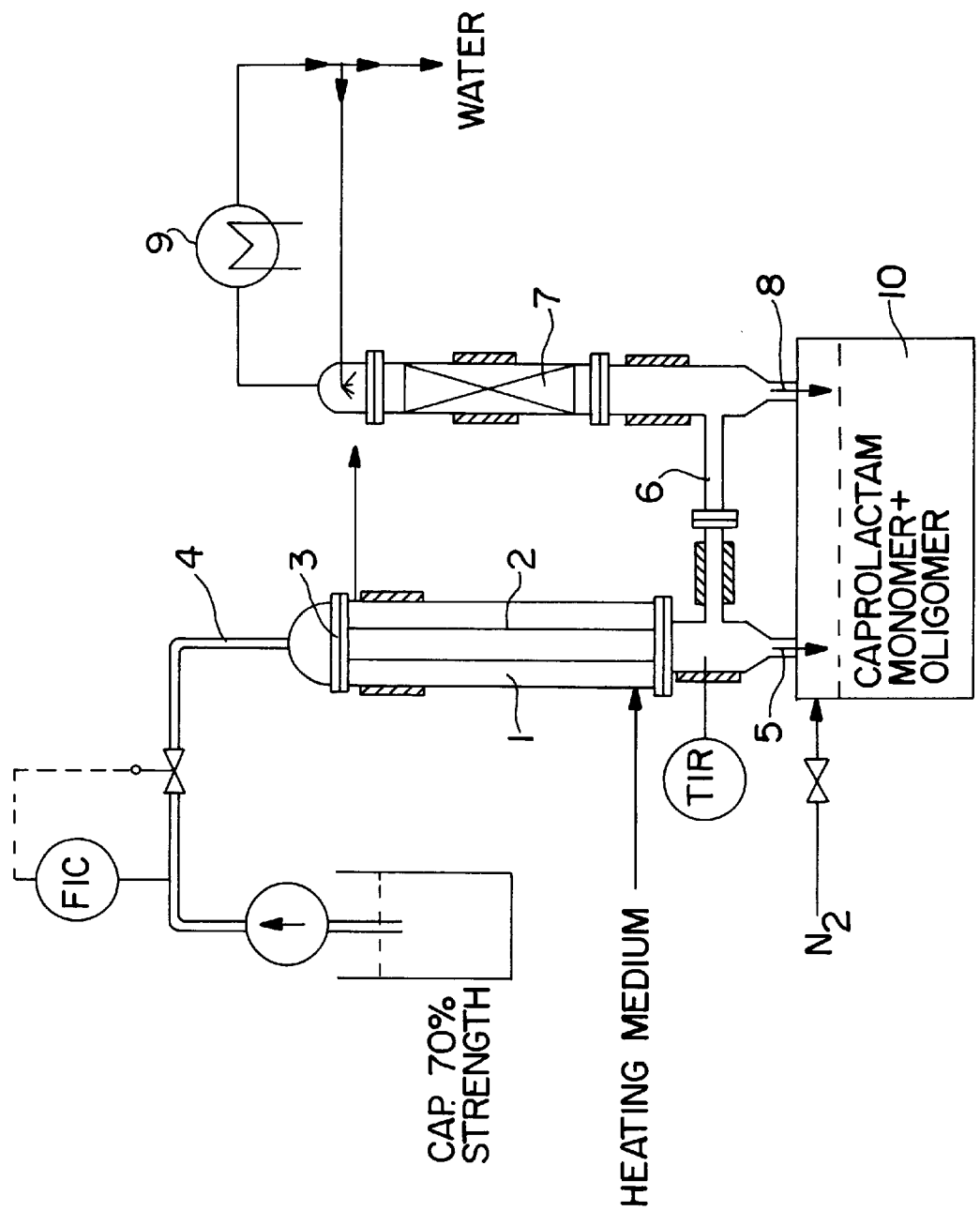

United States Patent

Egly et al.

[11] Patent Number: 5,962,681
[45] Date of Patent: Oct. 5, 1999

[54] RECOVERY OF CAPROLACTAM MONOMER AND OLIGOMER FROM AQUEOUS POLYCAPROLACTAM EXTRACTS

[75] Inventors: Horst Egly, Böhl-Iggelheim; Hans-Harald Hünger, Ellerstadt; Thomas Sauer, Dirmstein, all of Germany

[73] Assignee: BASF Aktiengesellschaft, Ludwigshafen, Germany

[21] Appl. No.: 08/972,763

[22] Filed: Nov. 18, 1997

[30] Foreign Application Priority Data

Nov. 25, 1996 [DE] Germany ............... 196 48 747

[51] Int. Cl.⁶ .................................................. C07D 201/12
[52] U.S. Cl. ................................................................ 540/540
[58] Field of Search ............................................... 540/540

[56] References Cited

U.S. PATENT DOCUMENTS

| | | | |
|---|---|---|---|
| 3,658,810 | 4/1972 | Tanaka et al. | 260/239 |
| 4,107,160 | 8/1978 | Dicoi et al. | 260/239.3 |
| 4,311,642 | 1/1982 | Crescentini et al. | 260/239 |
| 4,350,630 | 9/1982 | Fuchs et al. | 260/239.3 |
| 4,795,571 | 1/1989 | Holzknecht et al. | 210/774 |
| 5,294,707 | 3/1994 | Kotek | 540/540 |
| 5,441,607 | 8/1995 | Fuchs et al. | 203/49 |
| 5,681,952 | 10/1997 | Sifiniades et al. | 540/540 |
| 5,700,358 | 12/1997 | Fuchs et al. | 203/31 |

FOREIGN PATENT DOCUMENTS

| | | |
|---|---|---|
| 65168 | 11/1982 | European Pat. Off. . |
| 137124 | 4/1985 | European Pat. Off. . |
| 4129076 | 3/1993 | Germany . |
| 88/04651 | 6/1988 | WIPO . |
| 97/34868 | 9/1997 | WIPO . |

*Primary Examiner*—Yogendra N. Gupta
*Assistant Examiner*—Bruck Kifle
*Attorney, Agent, or Firm*—Keil & Weinkauf

[57] ABSTRACT

The disclosure is a process for recovering caprolactam monomer and oligomer from aqueous polycaprolactam extracts by removing the inorganic contaminants present therein.

6 Claims, 1 Drawing Sheet

RECOVERY OF CAPROLACTAM MONOMER AND OLIGOMER FROM AQUEOUS POLYCAPROLACTAM EXTRACTS

The present invention relates to a process for recovering caprolactam monomer and oligomer by removing inorganic contaminants from aqueous polycaprolactam extracts.

Polycaprolactam is the most important polyamide. Its quality has to meet high expectations. As-polymerized polycaprolactam generally comprises from 10 to 15% by weight of low molecular weight fractions, which frequently cause undesirable effects in further processing or have an unfavorable effect on the quality of the finished products. For instance, caprolactam monomer and its low molecular weight oligomers have a distinctly plasticizing effect on the polymer. These low molecular weight fractions can be removed from the polycaprolactam by aqueous extraction (cf. v. Hopf, Müller, Wenger in Die Polyamide, p. 26, and also DRP 766120).

The resulting solutions of caprolactam and its low molecular weight oligomers generally further comprise inorganic contaminants. For instance, extracts of pigmented polycaprolactam comprise not only the pigments themselves but usually also oxides of silicon or of aluminum from the pigment coating layer, which are not removable by filtration. These inorganic contaminants have to be removed before the caprolactam monomer and oligomer can be recycled into the polymerization process.

Caprolactam monomer is generally recovered from these extracts by removing the water in customary evaporators and then distilling the caprolactam. This leaves the sparingly volatile oligomers and the inorganic contaminants behind in the distillation residue. The distillation residue can be subjected to an oligomer-splitting operation to recover the rest of the caprolactam. A disadvantage of this method of recovery turns out to be that the reaction conditions required for a depolymerization prove to be highly abrasive and corrosive for the depolymerizing equipment. In addition, the inorganic constituents act as a catalyst poison, so that the depolymerization stops being selective after some time. The depolymerizing vessels therefore have only short operating intervals before they have to be cleaned again.

It is an object of the present invention to provide a novel process for recovering caprolactam monomer and oligomer free from inorganic contaminants from aqueous polycaprolactam extracts without the need for a depolymerizing step.

We have found that this object is achieved by a process for recovering caprolactam monomer and oligomer by removing inorganic contaminants from aqueous polycaprolactam extracts, which comprises passing the aqueous extracts continuously through an evaporator in such a way that the inorganic contaminants become deposited on the heat exchanger surfaces of the evaporator.

According to the present invention, the aqueous polycaprolactam extract is passed continuously in thin films over the heat exchanger surfaces of the evaporator while the temperature of the heat exchanger surfaces is above the boiling temperature of the aqueous extract. The ratio of liquid volume to evaporator tube geometry is preferably such that the evaporator surface is at least partially dewetted. This is ensured in particular when the ratio for the liquid volume emerging from the evaporator exit is below 200 l/(m·h), preferably within the range from 30 to 100 l/(m·h).

In a particularly preferred embodiment of the process of this invention, temperature and liquid volume are such that the evaporator effluent is a virtually anhydrous caprolactam monomer/oligomer melt. This preferably requires temperatures at the heat exchanger surfaces of the evaporator of above 220° C., especially above 235° C. The process of the invention is preferably carried out at atmospheric pressure or at a slight superatmospheric pressure, but it can also be carried out at reduced pressure.

The process of the invention can in principle be carried out with any evaporation technology in which the liquid to be evaporated is passed in thin films over heat exchanger surfaces. This includes plate film evaporators, falling-stream evaporators or falling-film evaporators (see also Ullmann's Enzyklopädie der technischen Chemie, 4th Edition, Vol. 2, p. 656 et seq.). However, commercially available falling-film evaporators are preferred. Heating is by steam or other heat transfer media according to technically customary methods.

The bulk of caprolactam monomer and oligomer is obtained in the evaporator effluent in the form of a highly concentrated solution or a melt, preferably having a water content<7% and especially<2%, based on the effluent. To recycle the caprolactam entrained in the course of the evaporation of the water, the vapors can subsequently be fractionated according to customary techniques, for example by means of columns. To avoid oxidation effects, it is preferable to flush all feed and discharge lines and also stock reservoir and collecting vessels with an inert gas, preferably nitrogen.

The deposited inorganic constituents are cleaned off the heat exchanger surfaces according to customary methods, for example by spraying with a sharp jet of water or by brushing.

The process of the invention is suitable for freeing customary polycaprolactam extracts as obtained in the production of caprolactam from inorganic contaminants and to recover the caprolactam monomer and oligomer present therein. Preference according to the invention is given to extracts having caprolactam contents above 60% by weight, in particular those having from about 70 to 75% by weight. Such solutions are generally obtained by concentrating the aqueous polycaprolactam extracts according to customary evaporation techniques.

The caprolactam monomer and oligomer recovered by the process of the invention is sufficiently pure for recycling into the polymerization process.

The Example which follows illustrates the invention.

EXAMPLE (FIG. 1)

The falling-film evaporator 1 is equipped with evaporator tubes 2 (length 1.5 m; diameter 21 mm). The evaporator is heated with a liquid heat transfer medium. The upper tube sheet 3 is charged with from 3 to 7 l of 70% strength by weight aqueous polycaprolactam extract via feed line 4. The temperature in the evaporator is controlled in such a way that the caprolactam present in effluent 5 has a temperature within the range from 235° C. to 250° C. The vapors are passed via a vapor bridge 6 into a column 7. Here entrained caprolactam separates out and is withdrawn via discharge S. The water vapor is removed overhead and condensed by means of a condenser 9. Effluents 5 and 8 are transferred into the stock reservoir vessel 10 which is flushed with inert gas via a nitrogen line to avoid oxidation effects.

We claim:

1. A process for recovering caprolactam monomer and oligomer by removing inorganic contaminants from aqueous polycaprolactam extracts, which comprises passing the aqueous extracts continuously through an evaporator in such a way that the inorganic contaminants become deposited on the heat exchanger surfaces of the evaporator and the caprolactam monomer and oligomer is obtained in the evaporator effluent.

2. A process as claimed in claim 1, wherein the ratio of liquid volume to evaporator tube geometry is such that the evaporator surface is dewetted.

3. A process as claimed in claim 2, wherein the ratio of liquid volume at the evaporator tube exit to tube circumference is below 200 l/(m·h).

4. A process as claimed in claim 1, wherein the evaporator is a falling-film evaporator.

5. A process as claimed in claim 1, wherein the aqueous polycaprolactam extract comprises at least 60% by weight of caprolactam monomer and/or oligomer.

6. A process as claimed in claim 1, wherein the caprolactam monomer and/or oligomer leaving in the evaporator effluent is at above 235° C.

\* \* \* \* \*